United States Patent [19]

Mann

[11] 4,061,488

[45] Dec. 6, 1977

[54] PLANT TREATING MIXTURES AND METHODS UTILIZING SPORES OF *BACILLUS UNIFLAGELLATUS*

[75] Inventor: Elton W. Mann, Hershey, Pa.

[73] Assignee: Hershey Foods Corporation, Hershey, Pa.

[21] Appl. No.: 395,661

[22] Filed: Sept. 18, 1973

Related U.S. Application Data

[60] Continuation-in-part of Ser. No. 306,221, Nov. 13, 1972, abandoned, and Ser. No. 121,199, March 4, 1971, Pat. No. 3,819,829, and Ser. No. 367,749, June 4, 1973, Pat. No. 3,920,812, which is a division of Ser. No. 121,199, March 4, 1971, which is a division of Ser. No. 672,462, Oct. 3, 1967, Pat. No. 3,617,448, which is a continuation-in-part of Ser. No. 334,907, Dec. 31, 1963, abandoned.

[51] Int. Cl.$^2$ .................... A01N 21/02; A01N 15/00
[52] U.S. Cl. .................................. 71/77; 47/57.6; 71/79; 424/93; 424/115
[58] Field of Search ................ 424/93, 115; 71/77; 47/57.6

[56] References Cited

U.S. PATENT DOCUMENTS

| | | | |
|---|---|---|---|
| 2,258,319 | 10/1941 | Dutky | 424/93 |
| 3,150,062 | 9/1964 | Greenberg et al. | 424/93 |
| 3,285,748 | 11/1966 | Koonz et al. | 424/93 |
| 3,499,748 | 3/1970 | Fraser | 71/77 |
| 3,617,448 | 11/1971 | Mann | 424/115 |

*Primary Examiner*—V. D. Turner
*Attorney, Agent, or Firm*—Seidel, Gonda & Goldhammer

[57] ABSTRACT

Spores of *Bacillus uniflagellatus*, s.p.n. (ATCC 15,134) are applied to plant seeds, as by the use of a shaker bag, or adhesively, or applied to the soil adjacent the seed by being commingled with the seed in a drill box. Alternatively, the roots of seedlings or transplanted plants may be dippd in an aqueous suspension of the spores, or in the case of densely populated, established crops, such as strawberries, the spores may be sprayed on the leaves and washed into the soil containing the root systems, or the spores may be worked into the soil adjacent to the rootlets, as in the case of trees. Many plants when treated with this microorganism produce an increase in yield based on total harvested crops, and/or an increase in yield in terms of higher permissive strengths or density of planting, namely more plants per given unit of area, and/or increased resistance to plant diseases. Over-fertilizing with nitrogen yields an increase in protein with oats, corn, wheat, and barley treated with the spores of *Bacillus uniflagellatus*.

38 Claims, No Drawings

PLANT TREATING MIXTURES AND METHODS UTILIZING SPORES OF BACILLUS UNIFLAYELLATUS

CROSS-REFERENCE TO RELATED APPLICATIONS

This application is a continuation-in-part of my co-pending patent application Ser. No. 306,221, filed Nov. 13, 1972, now abandoned. The present application is also a continuation-in-part of my co-pending patent applications Ser. No. 121,199, filed Mar. 4, 1971, now U.S. Pat. No. 3,819,829, and Ser. No. 367,749, filed June 4, 1973, now U.S. Pat. No. 3,920,812. Ser. No. 367,749 is a division of Ser. No. 121,199, which is a division of Ser. No. 672,462, filed Oct. 3, 1967, now U.S. Pat. No. 3,617,448, which was a continuation-in-part of application Ser. No. 334,907, filed Dec. 31, 1963, now abandoned. The disclosures of each of said patent applications is incorporated herein by reference.

BACKGROUND OF THE INVENTION

The present invention relates to methods and materials for treating plants. More particularly, the invention is directed to methods for increasing the yields of crops and food constituents derived from plants by treating the plants with spores of *Bacillus uniflagellatus*. Unless otherwise stated, the term "treating plants" as used herein will be understood to include the treatment of plant seeds, plant seedlings, or full grown plants or plants in any stage of development.

The microorganism employed in the practice of my invention is designated *Bacillus uniflagellatus*. A culture of the organism is on deposit with the American Type Culture Collection (ATCC No. 15,134), and is available to the public from the American Type Culture Collection, 12301 Parklawn Drive, Rockville, Md. 20852.

The morphological and physiological characteristics of *Bacillus uniflagellatus* are set forth in detail in my U.S. Pat. No. 3,617,448, the disclosure of which is incorporated herein by reference.

Other published materials relating to *Bacillus uniflagellatus*, the disclosures of which are incorporated herein by reference, are my papers: *Bacillus uniflagellatus: Sp.N. Its Unusual Characteristics*, The Southwestern Naturalist 13(3), 349–352, Dec. 10, 1968; and *Inhibition of Tobacco Mosaic Virus By A Bacterial Extract*, Phytophathology, Vol. 59, No. 5, 658–662, May 1969.

U.S. Pat. No. 3,617,448 discloses that an antibiotic substance which is produced by *Bacillus uniflagellatus* can be advantageously used to treat plants to control various fungal and viral diseases of plants. For example, fusarium wilt and damping off can be controlled by soaking cotton seeds and peanut seeds in a viable culture of *Bacillus uniflagellatus*; root knot nematodes may be controlled by spraying an aqueous solution of the antibiotic on the leaves of tomato plants; or the antibiotic or a culture of the *Bacillus uniflagellatus* may be applied to the soil in which plants are being grown in order to control various diseases by absorption of the antibiotic through the plant root system.

My above-mentioned article *Inhibition Of Tobacco Mosaic Virus By A Bacterial Extract* describes in detail experiments in which local lesions from tobacco mosaic virus (TMV) were reduced by adding the bacillus to the soil of tobacco plants or adding extracts from the cultures of the bacillus to the soil or spraying the extracts on the leaves of the tobacco plants.

While the application of cultures of *Bacillus uniflagellatus* or the application of the antibiotic substance produced by *Bacillus uniflagellatus* has been found to produce excellent results in treating plants in various manners, it would be highly desirable to have a simpler and more economical method and material for treating the plants to achieve comparable results.

This invention has as an object the provision of an improved method for increasing the yield of crops and food constituents derived from plants.

This invention has as another object the increase in over-all weight of plants from a given amount of seed.

This invention has as still another object the increased yield in terms of higher permissive stress or density of planting for crops, namely more plants or crop per given unit of area of soil.

This invention has as still another object the increased yield of valuable food constituents derived from plants, such as protein.

This invention has as yet another object an improved method for improving the health of growing crops, and the avoidance of plant diseases.

This invention has as yet another object the provision of a mixture useful for the treatment of plants to increase yield and utilization of growth potential.

This invention has as yet another object the provision of seeds coated with spores of *Bacillus uniflagellatus*, and a method of adhesively securing spores of *Bacillus uniflagellatus* to the seeds.

BRIEF SUMMARY OF THE INVENTION

The above and other objects are accomplished by the method of the present invention in which spores of *Bacillus uniflagellatus* are either commingled with or adhesively secured to seeds prior to the planting of such seeds, and/or spores are planted with the seeds by being inserted into the drill box prior to, or during planting, or the spores may be worked into the soil adjacent to the rootlets, as in the case of trees. Alternatively, the roots of seedlings or transplanted plants may be dipped in an aqueous suspension of the spores. With densely populated, established crops, such as strawberries, the spores may be sprayed on the leaves, and then washed or otherwise deposited into the soil containing the plant root systems.

While pure spores of *Bacillus uniflagellatus* may be used to treat seeds, it is preferred to use the spores uniformly admixed upon a carrier, as hereinafter set forth.

In order to increase the yield of valuable food constituents, excess nitrogen may be added for foliar spray, or to the soil, as by over-fertilization of the soil with nitrogen-releasing components.

Throughout this specification, and the appended claims, when the spores are referred to, unless the meaning is clearly otherwise, the spores referred to are those spores of *Bacillus uniflagellatus* which after germination and growth on root exudate release antibiotic in contact with the roots of the plants being treated. Thus, not all spores of *Bacillus uniflagellatus* are active when contacted by the exudate from the roots of plants being treated. For example, when *Bacillus uniflagellatus* is grown in a chocolate by-products medium containing very high concentrations of glucose, such as about 30 grams glucose per liter, the spores produced from such media rarely, if ever, are efficacious for the treatment of plants, since they do not release antibiotic after germination and growth on contact with the exudates from the roots of the plants being treated. A chocolate by-products culture medium should preferably contain at least about 10 grams per liter of glucose to yield an appreciable amount of spores and antibiotic. A sugar, such as sucrose, which yields glucose on being split by the *Bacillus uniflagellatus* may be used in place of the glucose in the culture medium. In most media, sucrose is to be preferred to glucose, both because it is cheaper, and because the bacteria must split it before it can use the glucose. This minimizes the presence of excess glucose.

DETAILED DESCRIPTION

*Bacillus uniflagellatus* may be grown in a variety of nutrient media to yield the antibiotic referred to in patent 3,617,488. U.S. Pat. No. 3,617,488 discloses suitable carrot, and casamino acid media. Another suitable culture medium may be derived from chocolate manufacture by-products, such as presscake and expeller cake.

Presscake is a by-product of the confectionery industry. It is prepared by subjecting a mixture of chocolate and confectionery products, such as scrap candy, miswrapped candy bars from which cocoa butter has been pressed, to pressures of the order of 80 to 7000 psi and temperatures of 125° to 250° F., and then granulating the product. The ingredients will vary greatly depending on the starting materials but will normally include cane sugar, milk solids, cocoa, cocoa butter, peanuts and almonds. An example of one form of presscake may have an analysis of 12 weight percent protein, 7 weight percent fat, and 3 weight percent fiber, although the analyses will vary depending upon the raw material. The present major use of presscake is as animal feed.

Expeller cake is derived from cocoa shell fragments and dust from which cocoa butter has been expelled by temperature and pressure. Commercial equipment is available for obtaining expeller cake from lumps of whole unroasted cocoa beans, roaster clean-down and various shell fractions from the shelling process. The normal temperature used to obtain expeller cake are of the order of 200° to 350° F. Following pressurization, the expeller cake is granulated. Like presscake, expeller cake is a conventional material of commerce, and a by-product of the candy industry.

By way of example, and not by way of limitation, spores of *Bacillus uniflagellatus* which yield antibiotic on germination and growth on contact with exudates from the roots of the plants being treated may be derived from a chocolate by-product presscake and expeller cake nutrient medium as follows:

EXAMPLE A 650 grams of 100 mesh expeller cake, 100 grams of 100 mesh presscake, 2 grams of ammonium nitrate, and 2 grams of ammonium chloride were blended into 10 liters of distilled water with vigorous agitation. The resultant mixture was then sterilized by autoclaving at a pressure of 15 pounds per square inch gauge for over one hour. Thereafter, the medium was inoculated with a culture of *Bacillus uniflagellatus* with the medium being maintained at a temperature of 32° C. Air was bubbled through the inoculated medium (*Bacillus uniflagellatus* is aerobic) for from 12 to 14 days.

The mixture is then centrifuged to remove all solid materials.

The aqueous material from the centrifuge may then be extracted with ether for antibiotic production.

To retrieve the spores from the centrifuged bottom material, the bottom material is vacuum dried to a solid cake while at a temperature of 80° C. After drying, the hard cake is ground and sifted to the extent that it will pass through a 100 mesh screen. This material is fine enough to stick to seeds; if desired, other mesh sizes may be used, such as within a range of from 50 to 325 mesh.

Yet another method of producing spores of *Bacillus uniflagellatus* which yield antibiotic on germination and growth on contact with exudates from the roots of the plants being treated is set forth below:

EXAMPLE B 300 grams of 100 mesh expeller cake, and 100 grams of 100 mesh presscake are blended into 10 liters of distilled water, and the mixture thoroughly agitated to ensure complete diffusion of the solids throughout the liquid. The 10 liter mixture is then placed in a steam sterilizer at a pressure of between 15 and 20 psi for a period of ninety minutes.

Upon its removal from the sterilizer, and cooling to 32° to 34° C. it is inoculated with a sporulated culture of *Bacillus uniflagellatus,* as from an agar slant, which is melted by heat and poured into the water.

The mixture may be treated in a 12 liter flask by maintaining it at a temperature of 32° to 34° C. and agitating it and providing oxygen to it by bubbling filtered air through it for a period of 14 days. The temperature of 32° to 34° C. is to be preferred, although somewhat higher and lower temperatures may be used.

The mixture may then be centrifuged and the liquid removed for extraction for antibiotic recovery. The solids may be separated and dried, ground and sifted, and collected as a dust containing the spores.

Alternatively, the entire culture at the end of the 14 days may be passed through a spray drier, removing the water and recovering both the spores and the antibiotic in the form of fine dust. This latter procedure is to be preferred since it avoids the need for centrifuging, drying, grinding, sifting, and collecting.

Growth stimulators may be added to the expeller cakepresscake culture medium to increase the yield of viable cells of *Bacillus uniflagellatus.* I have found that an outstanding growth stimulator for *Bacillus uniflagellatus* in chocolate by-product media is peanut heart. Although whole peanuts perform as well as a growth stimulator as peanut hearts, the peanut hearts are to be preferred because of their far lower price. Thus, in many confections, it is desirable to separate the peanut hearts from the peanuts, due to the relative unpalatable taste and shortened shelf life of the peanut hearts. Separation of peanut hearts from peanuts may be accomplished by well-known commercial procedures which are presently employed in the confection industry. Peanut hearts and peanuts are not a growth stimulator for *Bacillus uniflagellatus* with carrot-based culture media.

To illustrate the growth stimulation affect of peanut hearts on *Bacillus uniflagellatus,* a comparison was made between a control culture medium of expeller cake, presscake, ammonium nitrate, and ammonium chloride, as set forth above in Example A, and an identical medium which also contained an aqueous peanut heart extract. The peanut hearts were present (although derived from an aqueous extract) to the extent of 4 weight percent peanut hearts based on the total solid components of the culture medium. With the control culture medium, an average of 16,920,000 viable cells per ml were obtained after 72 hours of fermentation at 32° C. while with the identical medium containing the peanut heart extract an average of 42,620,000 viable cells per ml were obtained after 72 hours of fermentation at 32° C.

A preferred method of producing spores of *Bacillus uniflagellatus* which yield antibiotic on germination and growth on contact with exudates from the roots of the plants being treated by using peanut hearts as a stimulator is as follows:

EXAMPLE C 400 grams of 100 mesh expeller cake, and 100 grams of 100 mesh presscake, and 137.5 grams of peanut hearts are blended into 11 liters of distilled water, and the mixture thoroughly agitated to ensure complete diffusion of the solids throughout the liquid. The 11 liter mixture is then placed in a steam sterilizer at a pressure of between 15 and 20 psi for a period of 90 minutes.

Upon its removal from the sterilizer, and cooling to 32° to 34° C. it is inoculated with a sporulated culture of *Bacillus uniflagellatus*, as from an agar slant, which is melted by heat and poured into the mixture.

The mixture may be treated in a 12 liter flask by maintaining it at a temperature of 32° to 34° C. and agitating it and providing oxygen to it by bubbling filtered air through it for a period of 14 days.

The mixture is then allowed to settle and the supernatant liquid decanted off for extraction and antibiotic recovery. The residue is passed through a spray drier removing the water and recovering both the spores and the antibiotic in the form of fine dust. This latter procedure is to be preferred since it avoids the need for centrifuging, drying, grinding, sifting, and collecting.

When the spores of *Bacillus uniflagellatus* are produced in accordance with any of the above described methods, the spores are recovered in a substantialy uniform dust or powder with the remains of the culture medium in which the spores were produced. This dust or powder provides an inexpensive, inert carrier which avoids the use of wastefully high concentrations of spores and assures more even distribution of available spores, protects the spores against abrasion when being used and is substantially non-toxic to plants and to the spores. The carrier protects the spores against excessive aeration, and may function as a lubricant if the mixture is dispensed from a drill box. In order to prevent the spores from germinating prior to treatment of plants, the water content of the combined spores and powdered carrier should be controlled so that it does not exceed 10 weight percent water. There is normally no economic justification to reduce the weight percent of the water to below 4 weight percent. By "weight percent water" as used herein is meant a determination obtained by comparing the initial weight to the weight after tray drying for 48 hours at 100° C. under a 27 inch vacuum (a vacuum equal to about 3 inches of mercury absolute pressure, or one-tenth atmosphere pressure).

In this manner, the spores will have a shelf life of in excess of one planting season. Thus, I have found that a substantialy uniform dispersion of between 24,000,000 and 29,000,000 spores per gram on the aforesaid carrier having less than 10 weight percent water, lost approximately 25% of its potency when stored for 6 months at room temperature in a capped container.

The carrier derived from the culture medium should be cheap, stable on storage, inert, and non-toxic to plants and to *Bacillus uniflagellatus*.

In order to provide an economical and effective mixture for treating plants, production of the spores should be controlled to yield approximately 100,000 to 300,000,000 spores per gram of the mixture which includes the spores and the inert dust or powdered carrier. Preferably, the mixture should contain approximately 3,000,000 to 50,000,000 spores per gram of mixture. The method of Example C above will produce on the average of about 29,000,000 spores per gram of the powdered mixture, and the spores constitute below about 0.5 weight percent of the mixture. I believe that there are about 325,000,000,000 to 350,000,000,000 spores in a gram of pure spores.

An analysis of the powdered mixture produced by the method of Example C above reveals the following:

| Ingredient | Weight Percent |
|---|---|
| Total fat | 9.76% |
| Total protein | 24.6 % |
| Total ash | 5.9 % |
| Total carbohydrates (calculated as starch) | 11.1 % |
| Total reducing sugars (calculated as glucose) | 1.25% |

A number of different methods may be used to treat the plants in order to achieve the advantages of the present invention. The appropriate method to be selected will depend upon the particular plant to be treated and the nature of the growing pattern of the plant. For example, if the seeds of the plant are sufficiently large, it will be most convenient to apply the spores to the seeds or mix the spores with the seeds prior to planting. On the other hand, if the seeds are too small to have the spores applied thereto, as in the case of tobacco, the spores and carrier may be mixed into the soil in which the seeds are to be planted. Where the plants are usually started in a greenhouse or other controlled environment and then transplanted to a field, the plants may be treated at the seedling stage by treating the root systems with an aqueous suspension of the spores. Still further, where established plants are being treated, the spores may be sprayed upon the leaves and washed into the soil or merely mixed directly into the soil immediately surrounding the roots.

While theoretically a single spore per seed of plant being treated should be efficacious, as a practical matter the minimum number of spores per seed of plant being treated is of the order of at least 25, and preferably at least 100 spores per seed, when the spores are being adhesively bound to the seed. Somewhat higher number of spores per seed are preferred as a minimum when the spores are carrier, and the seed are blended in a drill box.

The number of spores per seed which will give beneficial results is generally larger as the size of the seed increases, or is larger if the seed is smooth-surfaced. I have obtained efficacious results using approximately 37 spores per seed in the case of alfalfa, 200 to 250 spores per seed for wheat, 250 spores per seed for barley, 250 spores per seed for oats, 800 to 1000 spores per seed for corn, and 250 to 300 spores per seed for most other food crops.

The seeds being treated and/or the soils in which the plants being treated are grown may contain most common fungicides and herbicides. Thus, I have found that captan, a widely used fungicide consisting of N([trichloromethyl]thio)-4-cyclohexene-1,2-dicarboximide, sold by the Stauffer Chemical Company, Westport, Connecticut 06880, has no noticeable affect on the efficacy of treatment with the spores of *Bacillus uniflagellatus*. This is a significant advantage of the present invention, since it permits the present invention to be employed with commercially treated seeds that contain fungicides such as captan, or even mercury. However, certain herbicides are toxic to *Bacillus uniflagellatus*, such as "Vernam" produced by Stauffer Chemical Company, Westport, Connecticut 06880. "Vernam" is described in United States Letters Pat. No. 2,913,327, and its active ingredient is S-propyl dipropylthiocarbamate. Simple testing can be used to ascertain if a given fungicide or herbicide is inimical to the efficacy of the plant treatments of the present invention. Whether a given fungicide is inert to *Bacillus uniflagellatus* may be readily ascertained by routine testing well within the skill of one having ordinary skill in the microbiological art. I believe that there is an advantage in having on the seed commercial fungicide, which is substantially inert to *Bacillus uniflagellatus*. Thus, such commercial fungicide protects the seed until the spores of the *Bacillus uniflagellatus* germinate and commence releasing antibiotic on contact with exudates from the roots of the plants being treated.

Perlite should never be used in appreciable amounts in soils being used for the plant treatments of the present invention. Thus, I have found that the presence of perlite in the soils of plants being treated adversely affects the process of the present invention. I believe that this is due to the fact that antibiotic released by the *Bacillus uniflagellatus* is preferentially adsorbed on the perlite.

While I do not wish to be bound by any theory as to the mechanism of the present invention, it is my belief that exudates from the fine hairs of the roots of plants stimulate the spores to germinate, and the vegetative cells release antibiotic in the region of the root hairs. The vegetative cells are motile and move in the vicinity of the root hairs and release antibiotic. I believe that the antibiotic or some component(s) of it is efficacious as a root stimulator, and also as a fungicide, and as an insecticide, effective against insects, such as corn root worms in the case of corn, and green bugs in the case of wheat. Moreover, it permits a larger number of seeds to germinate and to realize their genetic potential. (The increase in yields of cereal type food crops due to increases in number of kernels, and/or in some instances, increase in size of kernels).

A variety of methods may be utilized to contact the seeds being planted with the spores of *Bacillus uniflagellatus* and carrier. These include tumbling a mixture of the seeds with the finely divided spores and carrier. Thereafter, the combined mixture may be planted together utilizing the same techniques normally utilized for planting the particular seed.

Yet another embodiment of the method of the present invention is to adhesively coat the spores and carrier onto the seeds of the plant. A variety of processes are available for adhesively coating seeds with materials. The adhesive that is to be utilized should preferably be substantially inert to, or not adhesively affect, either the spores or the seeds. A satisfactory method of achieving adhesive coating is the use of the adhesive and procedure of the so-called "EVERSHIELD" process of Cargill Seed Company of Minneapolis, Minnesota. Pursuant to this method, the *Bacillus uniflagellatus* spores derived from the finely divided centrifuged bottom material are uniformly admixed with the seeds and adhesively coated thereto by an inert adhesive. Suitable equipment for adhesively applying the spores to the seeds is available from Gustafson Manufacturing, Inc. of Hopkins, Minnesota. Using this procedure, it is possible to adhesively coat seeds of wheat with an average of 4,852 viable spores per seed from a finely divided centrifuged bottom material containing approximately 52,000,000 spores per gram, when the seeds were coated with the finely divided centrifuged bottom material in an amount equal to 4 ounces of finely divided centrifuged bottom material per 100 pounds of seed. Besides the Cargill "EVERSHIELD" process and adhesive, I have found dihydroxy ethyl cellulose to be a satisfactory adhesive when used in amounts conventionally used for seed coatings.

For rice seed, which is aerially sprayed onto a liquid-covered field, a conventional sinker, such as sand, may be adhesively secured to the seed, so that the seed does not float on the water.

As indicated above, plants which are started in hot houses or controlled environments may be treated as seedlings when they are transplanted to open fields for maturation. This treatment may comprise dipping the seedlings into or spraying the seedling root systems with an aqueous suspension of the spores and carrier. I have successfully used a suspension containing 50 grams of spores and carrier having 29,000,000 spores per gram in a liter of water. Suspensions of 50 grams of spores and carrier per liter of water over the range of 100,000 to 300,000,000 spores per gram are efficacious for the treatment of seedlings while suspensions of spores and carriers in water containing about 50 grams per liter of from 3,000,000 to 50,000,000 spores per gram are preferred. It is preferred not to prepare this suspension more than 24 hours prior to use since the high water level of the suspension may cause the spores to start germinating.

Seedling treatments of this sort are particularly useful with truck garden food crop plants, such as tomatoes and peppers. This method may also be used with non-food crop plants, such as tobacco, ornamentals, or shrubbery.

A further, but less efficient method of treating the plants, comprises mixing the spores into the soil immediately surrounding the root system of the plant, and preferably adjacent to the rootlets, which in the case of trees are generally in the peripheral portions of the roots around the drip line edge of the leaves. The method is less efficient since many of the spores will probably be wasted. I have obtained improved fruit, such as peaches, devoid of blemishes, when applying the spores adjacent to the roots of the tree, and then washing the spores into the soil near the roots. Alternatively, a suspension of the spores in water may be injected under high pressure into the soil adjacent to the roots of the tree. Thus, it is believed that the beneficial results of the present invention are achieved when the spores germinate and the motile vegetative cells secrete the antibiotic derived from *Bacillus uniflagellatus* as a result of the presence of exudates from the roots. That is, a symbiotic relationship is apparently set up between the germinated spores and the root systems of the plant.

A still further method of treating the plants, which may also be somewhat inefficient, consists of spraying the spores and carrier onto the leaves of the plants and then washing the spores and carrier into the soil immediately surrounding the plants. Such a method is particularly advantageous for well established and densely populated crops, such as strawberries, and perennials, such as boysenberries, raspberries, blueberries, rhubarb and blackberries.

The present invention may be used on rice when the rice is planted into water-covered ground from the air. Under such circumstances, a somewhat higher concentration of spores should be utilized. By way of example, 6 to 7 ounces of spores containing 29,000,000 spores per gram per 100 pounds of rice seed is preferred.

The method of the present invention produces an increase in yield in total plant weight, and/or an increase in yield in terms of higher permissive strengths or density of planting, and/or increased resistance to plant diseases with at least the following food plants: barley, rice, wheat, corn, oats, bush beans, alfalfa, lettuce, castor beans (the source of castor oil), melon, strawberries, peaches, boysenberries, avocado, raspberries, peas, onion, rhubarb, blackberries, blueberries, zucchini, radishes, carrots, brussel sprouts, cucumbers, peanuts, pepper, tomatoes, cantaloupe, Garbanzo beans (chick peas), Irish potatoes, sorghum, cotton, mushrooms, cocoa, soy beans, and citrus fruits such as oranges, lemons, grapefruit and limes. The spores of *Bacillus uniflagellatus* may be feasibly adhesively secured to the seeds of each of the foregoing plants other than strawberries, peaches, boysenberries, raspberries, rhubarb, blackberries, blueberries, Irish potatoes, mushrooms, and cocoa. I have also demonstrated the advantageous results with tobacco plants, pyracantha, many house plants, and flowers, such as roses, African violets, begonias, poinsettia, and rubber plants.

On the basis of fragmentary testing, I have not been able to demonstrate efficacious results with all plants. In particular, my testing to date has revealed no positive (or negative) effects with plants having a single large taproot, with no appreciable branching of the root, such as sugar beets, table beets, and some types of carrots and radishes. It is my belief that the root exudates are unsuitable to support the *Bacillus uniflagellatus* with plants having a single large taproot, and little branching.

In addition, my testing to date has revealed no positive (or negative) effects with sweet potatoes, papaya, parsley and marigolds.

When an increase in nitrogen in the soil is present over that normally used to cultivate the plant, I have observed an increase in valuable food constituents derived from the plant, namely protein, with wheat, barley, corn, and oats. The amount of excess nitrogen in the soil which yields an increase in protein content of the grain varies depending on the type of plant, strain of seed, soil, time of application of fertilizer, and weather conditions. Moreover, there is an economic balance between the cost of the excess fertilizer and the value of the protein increase. The amount of excess nitrogen that should be used in a given instance to achieve a desired result may be readily determined by routine testing within the skill of one having ordinary skill in agriculture. For example, I have found that foliar spray nitrogen fertilizer (Agway) applied in the early spring at 40 pounds per acre following barley planted with *Bacillus uniflagellatus* the previous fall produces both an increase in yield and an increase of the protein content of the grain. The effect of fertilizing with excess nitrogen, as by foliar spraying with nitrogen fertilizer, to increase the amount of protein is most pronounced with barley. Indeed, there is sometimes an increase in protein without excessive nitrogen being present with wheat and barley due to the control of parasitic fungi by the *Bacillus uniflagellatus*. Such parasitic fungi attack algae which fix nitrogen.

The invention may be more fully understood by reference to the following examples. It is to be understood that the examples are merely for illustration and are not for the purpose of limitation.

EXAMPLE 1

Barley was planted on 29 acres of ground, divided into 11 plots as set forth below. These plots were indistinguishable as to soil composition. Plots 1, 2, 3, 4 and 5 were top dressed with 40 pounds of nitrogen per acre over and above the fertilizer used in the remaining plots. Plots 1, 10 and 11 were the control plots. The planting rate is given in pecks of seeds, with 10 pecks of seeds equaling 2 and ½ bushels of seeds. The yield is given as bushels per acre.

| Plot No. | Acres | Planting Rate | Yield/A | Protein Analysis* | Protein Analysis* |
|---|---|---|---|---|---|
| 1 | 2½ | 10 pk – 2½ bu. | 58.3 bu. | 10.26 | 10.91 |
| 2 | 2½ | 10 pk – 2½ bu. | 66.6 bu. | 9.69 | 10.53 |
| 3 | 2½ | 11 pk – 2¾ bu. | 78.0 bu. | 10.38 | 11.34 |
| 4 | 2½ | 12-½ pk – 3 + bu. | 68.0 bu. | 9.75 | 10.51 |
| 5 | 2½ | 14 pk – 3½ bu. | 72.4 bu. | 8.76 | 9.38 |
| 6 | 2½ | 14 pk – 3½ bu. | 59.6 bu. | 7.83 | 9.08 |
| 7 | 2½ | 12-½ pk – 3 + bu. | 58.8 bu. | 7.84 | 9.15 |
| 8 | 2½ | 11 pk – 2¾ bu. | 52.7 bu. | 7.98 | 8.01 |
| 9 | 2½ | 10 pk – 2½ bu. | 53.45 bu. | 7.49 | 8.73 |
| 10 | 2½ | 10 pk – 2½ bu. | 54.9 bu. | 7.83 | 8.87 |
| 11 | 2½ | 10 pk – 2½ bu. | 54.9 bu. | 8.84 | 8.57 |

By a comparison of plot 1 with plots 10 and 11, the effect of the nitrogen is seen as about 3.4 bushels per acre. By a comparison of plots 6, 7, 8 and 9 vs. plots 10 and 11, the effect of the *Bacillus uniflagellatus* is seen as about 1.2 bushels per acre. The combinative effect of the *Bacillus uniflagellatus* and the top dressing with nitrogen may be seen by a comparison of plots 2, 3, 4 and 5 vs. plots 10 and 11, and equal to about 16.3 bushels per acre. The increase in the density of planting plus the effect of the *Bacillus uniflagellatus* and the nitrogen top dressing is seen by a comparison of plot 3 vs. plots 10 and 11, and equals about 23.1 bushels per acre.

EXAMPLE 2

Six different varieties of Minnesota wheat were used in this example, with precisely 20 seeds of each variety planted in each of 6 pots, each 9 inches in diameter and filled to 2 inches of the top with field top soil. Three of the plantings were kept as a control. Three of the plantings were treated by dusting the seed in a plastic bag with 0.5 g. of *Bacillus uniflagellatus* spores at 54 million spores per gram. All 36 pots were positioned on a greenhouse bench and watered as required. After 102 days, the entire plants, including roots from each pot, were harvested, the roots were washed thoroughly and the plants bundled with rubber bands. The bundles were placed on paper towels and allowed to dry at greenhouse temperature. The bundles were turned twice each day to equilibrate and increase the drying rate. After 72 hours, each bundle of wheat plants was weighed and the results recorded.

Upon removing the plants from the pots, it was immediately apparent that the root mass of the treated plants was more extensive than those of the controls. After drying, the total weights of each bundle were as follows:

| Variety | Control | | | Treated | | |
|---|---|---|---|---|---|---|
| Spring Wheat "Z" | 23.4 | 22.6 | 20.2 | 21.5 | 29.0 | 24.7 |
| Durham Wheat | 19.1 | 17.7 | 23.5 | 28.3 | 24.3 | 17.1 |
| Spring Wheat "Y" | 36.6 | 29.4 | 36.9 | 41.2 | 39.1 | 31.9 |
| Northern Spring | 33.8 | 34.2 | 42.6 | 43.7 | 44.1 | 37.4 |
| Winter Wheat | 33.4 | 37.7 | 37.0 | 42.0 | 37.7 | 39.2 |
| Spring Wheat "X" | 25.4 | 24.1 | 20.5 | 32.4 | 29.2 | 27.4 |

Statistical analysis of the above table shows a probability of effect exceeding 99%. Plants depend on their root systems for nutrition, support and moisture. The better the root system, the more nearly a plant can approach its genetic potential. These plants were stressed by an excessive planting rate. They are probably also stressed by the natural microflora of the soil.

EXAMPLE 3

A greenhouse bench 3 × 4 feet was filled to a depth of 4.5 inches with a mixture of 2 parts top soil and 1 part sand. Three rows 3 feet long were planted with commercially treated (Ceresan, a compound of Mercury) Red Coat Wheat, at a rate of 60 seeds per row. In the same bench 3 rows of the same seed were planted after dusting with 0.5 g. of spores of *Bacillus uniflagellatus* at 54 million spores per gram. The seeds were evenly spaced using tweezers to avoid excessive competition between plants. The plants were subjected to normal watering with 5 intervals of drought to the point of serious wilting. After 85 days, the soil mixture was again allowed to dry out. The plants were dug up and the roots were thoroughly washed. After 4 days of bench drying, they were weighed and the weights recorded as :

| Control Weights | Treated Weights |
|---|---|
| 34.4 g. | 55.1 g. |
| 32.5 g. | 56.1 g. |
| 48.4 g. | 73.1 g. |

Two adverse factors are operable in this experiment. First, the mixture of top soil to sand at 2 parts to 1 could not be expected to be optimum for wheat production. Secondly, the cycles of drought, though similar to what might be expected on the high plans of the "Wheat Belt" may have been unduly severe. There is a possibility of intermingling of the roots between the inside control row, showing 48.4 g., and the inside treated row, showing 55.1 g. In this instance the massive root systems of the treated plants compared to the controls were quite obvious.

EXAMPLE 4

To substantiate the results in Example 3 another bench in the greenhouse 3 × 4 feet was filled to a depth of 4.5 inches with a 2-1 mixture to top soil and sand. An aliquot of the same Red Coat variety wheat was planted at the same rate of 60 seeds to a 3-foot row. Watering was maintained equally over the entire bench, but only 3 cycles of drought were included. Again, after 85 days, the soil mixture was allowed to dry out. The plants were dug up and the roots thoroughly washed. After 4 days drying on the greenhouse bench the weights were recorded as:

| Control Weights | Treated Weights |
|---|---|
| 74.3 g. | 103.0 g. |
| 66.1 g. | 93.4 g. |
| 76.6 g. | 101.3 g. |

Under the more moderate drought stress of this experiment compared to that of Example 3, the total plant weights are perhaps more reasonable. Interesting, perhaps, is the fact that the average increase of plant weight in Example 3 is 69%, while the average increase in Example 4 is only 47%. Interpretation of this variable might conclude that the greater the stress the plant in under, the greater the benefit from the treatment with *Bacillus uniflagellatus.*

EXAMPLE 5

To investigate the effect of *Bacillus uniflagellatus* as a control of *Fusarium roseum*, a culture was obtained from Penn State University designated R-461. Three petri dishes 90 mm. diameter were prepared with Potato Dextrose Agar and inoculated with the fungus. After growth completely covered the surface, the contents of all dishes were blended into 500 ml. of 0.2% peptone broth. Further dilution with 1500 ml. of distilled water provided the soil inoculum. A greenhouse bench 4 × 4 feet was filled to a depth of 4-½ inches with top soil. No sand was included. One-half of the bench was inoculated with the Fusarium culture. Six rows 4 feet long were planted with 30 grams of the same commercially treated Blue Boy Wheat. The planting was at right angles to the Fusarium inoculation so each row was ½ in the inoculated soil and ½ in the uninoculated soil. During the 55 day growth period the plants were subjected to 3 cycles of drought. After 55 days, the plants were dug, the soil removed dry and the plants weighed. They were then thoroughly washed and dried for 6 days and weighed again as recorded:

| Fresh Weights in Grams | |
|---|---|
| Control | Treated |
| 196.2 | 211.5 |
| 191.1 | 246.5 |
| 186.0 | 251.0 |
| 163.5 | 344.0 |
| Dry Weights in Grams | |
| Control | Treated |
| 122. | 120. |
| 103. | 130. |
| 118. | 124. |
| 111. | 174. |

The drought cycles in this experiment were limited in degree because the Fusarium inoculated portion of the control rows always was the first to wilt and continued withholding of moisture would certainly have caused their death.

EXAMPLE 6

A previous experiment with oats had shown little effect of the *Bacillus uniflagellatus* treatment since there was no detectable stress on the plants. This experiment was designed to test the effect of the *Bacillus uniflagella-*

*tus* under the stress of plant density. A greenhouse bench 4 × 4 feet was filled to a 4½ inch depth with top soil. Three rows of commercially treated oat seed were planted at the rates of 15, 30 and 60 grams per row. Identical seed and planting rates were used in 3 Bacillus treated rows. Four cycles of drought were included in the growing period of 61 days. The plants were dug, washed, dried and weighed. The weights are recorded:

| Row Number | Planting Rate Grams/4' Row | Dry Weight of Plants |
|---|---|---|
| 1. Control | 60 | 293 |
| 2. Control | 30 | 152 |
| 3. Control | 15 | 190 |
| 4. Treated | 15 | 251 |
| 5. Treated | 30 | 209 |
| 6. Treated | 60 | 310 |

Optimum yields require optimum density of plant populations. With any plant treatment, a new planting rate may be expected. If the full magnitude of efficacy is to be reached, appropriate planting rates of Bacillus treated seed will have to be determined by routine testing.

EXAMPLE 7

A greenhouse flat 14 × 20 × 2½ inches was filled with top soil. Eighteen grains of corn, Pioneer 3304N, were planted in one row the length of the flat. Eighteen similar grains were treated by dusting with *Bacillus uniflagellatus* spores and planted in the same flat. Regular watering with no drought cycles was maintained, and growth was continued for 30 days. The plants together with their roots were dug up, washed and weighed after 24 hours drying. The results were:

| Control | Treated |
|---|---|
| 17 plants 172.5 g. | 17 plants 192.5 g. |

By chance, one seed in each group failed to germinate leaving 17 corn plants in each group. In this instance the most noticeable difference between the treated and control groups was in the thickness of the stalk. Root masses were not excessively different.

EXAMPLE 8

To further examine the efficacy of *Bacillus uniflagellatus* on corn, a greenhouse bench 4 × 4 feet was filled with top soil to a depth of 4½ inches. Forty seeds were planted in each row. Two rows were untreated and maintained as a control and two rows were treated by dusting with the Bacillus spores. After 41 days the plants were dug and the soil removed from the roots dry. The plants were weighed. They were then washed thoroughly and dried for 48 days. The results were:

| Fresh Control | Fresh Treated |
|---|---|
| 456.0 g. | 655.3 g. |
| After 48 Days During | |
| 93.5 g | 123.0 g. |

In this instance also, of 80 seeds planted, 3 failed to germinate leaving exactly 77 plants in each group. Although the treated group was slightly taller and their root mass slightly greater, the major difference was in the thickness of the stalk.

EXAMPLE 9

A short-term growth experiment with wheat was conducted to determine how soon a measurable effect of *Bacillus uniflagellatus* could be observed.

A greenhouse bench 4 × 4.5 feet was filled to a depth of 4½ inches with top soil (Hagerstown Silt Loam). Commercially treated seed at 30 grams per row were planted on the 4.5 foot length of the bench in 3 rows. Three parallel rows were treated with Bacillus spores by dusting in a plastic bag with 0.5 g. of Bacillus spore dust at 54 million spores per gram. Normal watering procedures with no drought cycles were continued for 9 days. The plants were permitted to grow for 5 more days. After the 14 day growing period, the plants were dug up in segments of 18 inches or ⅓ of a row. The plants were bunched, washed, dried for 72 hours and weighed. The results were for the row segments:

Control: 16.2 – 15.1 – 8.2 – 11.6 – 15.4 – 7.7 – 10.2 – 15.8 – 8.6
Treated: 10.8 – 17.5 – 8.9 – 15.5 – 17.8 – 11.1 – 21.2 – 16.6 – 10.7

Statistical analysis of these figures reveals a probability factor of over 95%. The planting rate was not particularly excessive although the results show it was not exactly evenly distributed. Since the greatest danger to seedlings is in their early days of growth, it is reassuring to observe the early effect of the Bacillus.

EXAMPLE 10

A greenhouse flat 4 × 20 × 2½ inches was filled with top soil. Two rows of beans were planted 9 per row on one side of the flat as a control. Two rows of the same number were planted after dusting with the Bacillus spores. Regular watering was maintained. The harvest of string beans was conducted over a period of 35 days. Weights of each harvest were recorded:

| Harvest Sequences | Control | Treated |
|---|---|---|
| 1 | 21.8 | 26.4 |
| 2 | 24.0 | 24.3 |
| 3 | 17.1 | 26.8 |
| 4 | 9.1 | 12.1 |
| 5 | 5.5 | 17.7 |
| 6 | 17.5 | 30.8 |
| TOTAL | 95.0 | 138.1 |

Tasting of the beans indicated they were delicious.

EXAMPLE 11

Six plastic pots measuring 11 inches in diameter and 12 inches high were prepared by cutting a 1-inch hole in the bottom, adding 2½ inches of broken stone, filling to 1 inch of the top with top soil. Twenty seeds of alfalfa were planted in each of 3 of the pots. Twenty seeds were covered with Bacillus spore dust using tweezers and planted in each of 3 other pots. The pots were maintained in close proximity on the greenhouse bench to minimize position effect.

After 86 days, the plants were cut off near the soil line and bundled and dried for 5 days.

The weight of dried alfalfa hay from each pot was recorded:

| Control Pot # | Weight of Dried Hay | Treated Pot # | Weight of Dried Hay |
|---|---|---|---|
| 1 | 52.4 | 1 | 71.2 |
| 2 | 35.1 | 2 | 54.0 |
| 3 | 48.7 | 3 | 68.0 |

EXAMPLE 12

A plastic 1-pound bag of Garbanzo beans (chick peas) was purchased at a local market. A greenhouse bench 4 × 4 feet filled to a depth of 4½ inches with top soil was prepared. Four rows of beans planted 4 inches apart constituted the control. Four rows with equal numbers were planted with beans dusted with Bacillus spores. Normal watering was continued until the plants averaged about 6 inches in height. Two drought cycles were included prior to maturity.

Although germination was not good, just under 50%, there was 25% greater germination in the treated than in the control group. Damping off (water soaking and plant depth) was prevalent among the untreated controls. Pre-emergence damping off might have been involved in the apparent difference in germination.

After the 2 drought cycles, the plants were maintained until maturity. Perhaps because of greenhouse conditions or some other unknown, none of the plants exhibited normal bushing growth and remained spindly or anemic. The beans were harvested and weighed. Beans from the control group weighed only 26.0 g., while those from the Bacillus treated seed weighed 37.5 g.

EXAMPLE 13

Two 7-inch plastic pots were filled with top soil to within 2 inches of the top. Twelve castor beans were spaced equally over the surface of the soil in each pot. Then with tweezers a pinch of spore dust of *Bacillus uniflagellatus* was placed on the 12 seeds of the treated group.* Another 1-½ inches of soil was added to each pot to thoroughly cover the beans. Routine watering was continued with no drought cycles.

In the control pot, 4 castor beans sprouted, and one of them damped off (became water soaked) at the soil line, fell over and died a few days after coming up. In the treated pot 11 castor beans sprouted. All of them remained vigorous until they became pot-bound and were transplanted as a lawn border where they reached a height of over 9 feet.

EXAMPLE 14

A 1528 gram sample of Colusa Rice seed was divided into 2 equal portions. One portion was treated with 5 grams of spore dust of *Bacillus uniflagellatus*. Each portion was then subdivided into 3 equal portions of nearly 255 grams. All 6 sub-samples were planted in separate rows in a plot of garden soil. After 135 days, all the plants were cut at the ground line, bunched and dried for 4 days on a greenhouse bench and weighed as follows:

| Treated | | Control | |
|---|---|---|---|
| Row # | Weight | Row # | Weight |
| 1 | 513.0 | 1 | 155.0 |
| 2 | 597.3 | 2 | 132.3 |
| 3 | 278.1 | 3 | 53.0 |

*Castor beans are too slick to retain the *Bacillus* dust.

The plants grew during the exceptionally cool and dry weather following Hurricane Agnes in 1972. These conditions were highly unfavorable to rice growing. Many plants, even some from the treated seed, withered and died while still quite young. Whatever happened to the control rice also affected the treated rice, but to a lesser extent. The rice was cut before maturity because a heavy frost was expected and arrived the night following the cutting. Little or no grain had been produced.

EXAMPLE 15

A 1971 field test of corn (Agway Ind 654) was planted at a rate of 23,500 seeds per acre in 38-inch rows spacing about 7 inches between plants in the row. Spore dust of *Bacillus uniflagellatus* at 4 ounces per bushel had been applied to the seed in a treating drum several days prior to planting. Treated seed was planted in about half of the field and untreated seed in the remainder as a control. Seven random samples of 30 feet of row were taken from the treated and seven more from the control plot. The ear count and total weight of each sample was recorded as:

| | Control | | Treated | |
|---|---|---|---|---|
| Sample # | Ears | Weight | Ears | Weight |
| 1 | 30 | 15.25 | 40 | 20.25 |
| 2 | 33 | 16.00 | 37 | 18.00 |
| 3 | 32 | 15.50 | 39 | 20.50 |
| 4 | 35 | 16.75 | 36 | 17.25 |
| 5 | 30 | 14.50 | 38 | 19.75 |
| 6 | 34 | 16.75 | 39 | 20.50 |
| 7 | 36 | 18.25 | 40 | 21.50 |
| Totals | 231 | 113.00 | 269 | 137.75 |

The plant population in the control plot was 15,130, while the plant population in the treated area was 17,423. In spite of the proximity stress in the treated plot, the average ear weighed 0.512 lbs., while the control ears averaged only 0.489 lbs. Overall the test shows an increase of nearly 22% in corn production.

EXAMPLE 16

A field test of corn (Funks 4697) was planted in another field at the same rate and spacing as in Example 15. Again, seven samples were taken from each plot to measure the effect of *Bacillus uniflagellatus*. The results were as follows:

| | Control | | Treated | |
|---|---|---|---|---|
| Sample # | Ears | Weight | Ears | Weight |
| 1 | 36 | 17.50 | 40 | 21.25 |
| 2 | 42 | 21.00 | 42 | 20.75 |
| 3 | 39 | 18.75 | 43 | 22.50 |
| 4 | 44 | 23.00 | 43 | 22.25 |
| 5 | 40 | 19.50 | 44 | 23.00 |
| 6 | 38 | 20.25 | 40 | 19.75 |
| 7 | 41 | 19.75 | 42 | 21.25 |
| Totals | 280 | 139.75 | 294 | 150.75 |

The plant population in this instance was 18,300 per acre for the control plot and 19,250 per acre for the treated plot. Again, although the plants were more numerous in the treated plot the average ear weight was 0.513 lbs. for the treated and 0.498 lbs. for the control. This field was entirely flat bottom land and while there was little stress during the growing season (1971), the treatment produced nearly 8.0% increase in corn yield.

EXAMPLE 17

Another corn test (1971) using *Bacillus uniflagellatus* was conducted using Pioneer 3369A seed. The row spacings were 30 inches and the planting at about 9 inches within rows making a seeding rate of 23,500 seeds per acre. Again, seven samples were taken at random over the treated and control plots with the results as follows. Treatment was applied in a drum prior to planting at a rate of 4 ounces per bushel.

| Sample # | Control | | Treated | |
|---|---|---|---|---|
| | Ears | Weight | Ears | Weight |
| 1 | 32 | 15.45 | 37 | 19.25 |
| 2 | 31 | 15.25 | 36 | 17.75 |
| 3 | 30 | 14.50 | 35 | 18.00 |
| 4 | 32 | 16.25 | 39 | 20.00 |
| 5 | 34 | 16.75 | 38 | 19.50 |
| 6 | 35 | 17.25 | 39 | 20.25 |
| 7 | 31 | 14.25 | 38 | 19.75 |
| Totals | 225 | 110.20 | 262 | 134.50 |

Plant populations were 18,585 per acre for the control and 21,549 per acre for the treated plot. Although the plant density was markedly greater in the treated plot, the average ear weights for the treated corn was 0.513 lbs. per ear, while the control ears averaged 0.489 lbs. per ear. The overall yield in this instance was increased by 22% by the treatment.

EXAMPLE 18

A 1972 corn test was deliberately stress planted by increasing the planting rate to 28,000 seeds per acre. Three plots of 40 rows each were planted in the same field. One plot without treatment was used as a control. One plot was treated with spore dust of *Bacillus uniflagellatus* at a rate of 4 ounces per bushel. The third plot was treated with spore dust at a rate of 6 ounces per bushel. The treatment was applied in the planter box with the seed and mixed. The effects were measured at harvest by taking 1/1000 of an acre samples counting all stalks and harvesting all ears and weighing each sample. Five samples were taken in a 2-1-2 pattern from each plot and the results recorded as:

| Control | | | 4 Oz. Treatment | | | 6 Oz. Treatment | | |
|---|---|---|---|---|---|---|---|---|
| Stalks | Ears | Weight | Stalks | Ears | Weight | Stalks | Ears | Weight |
| 25 | 23 | 102 | 26 | 25 | 116 | 27 | 26 | 200 |
| 24 | 25 | 116 | 26 | 27 | 120 | 26 | 25 | 154 |
| 24 | 23 | 96 | 25 | 23 | 126 | 23 | 24 | 172 |
| 23 | 24 | 100 | 24 | 23 | 134 | 28 | 28 | 160 |
| 24 | 23 | 142 | 27 | 28 | 144 | 25 | 25 | 166 |
| Av. 24 | 23.6 | 111.2 | 25.6 | 25.2 | 128.0 | 25.8 | 25.6 | 170.4 |

The intentional planting stress was compounded by the fact that the entire plot was on a gentle slope and the soil was more shale than loam. Hurricane Agnes in 1972 further stressed the plants by excessive leaching of the nutrients from the soil. This was followed by nearly 7 weeks of serious drought. Since all plots sustained equivalent exposure to multiple stress the effect of the seed treatment with *Bacillus uniflagellatus* in this example is shown to be a 15.1% increase in corn yield with a 4 ounce per bushel application, and a 53% increase in corn yield with a 6 ounce per bushel application. Many ears in both treated and control samples were empty or poorly seeded due to the drought at the time of pollination, but every ear on every stalk in every test was included in every sample. An average of less than 6 ounces per ear for the treated corn is very poor, but it is far better than the control.

EXAMPLE 19

In 1971 a field test of wheat (Red Coat) was conducted with 4.85 acres of seed treated with *Bacillus uniflagellatus* spore dust at a rate of 4 ounces per acre. A control plot in the same field of 27.15 acres was untreated and planted at the same rate with the same drill. At harvest, the total grain from each test was weighed and recorded as:

| Control | Treated |
|---|---|
| 37.76 bu./acre | 42.15 bu./acre |

The difference amounts to 4.39 bushels per acre or an 11.62% increase attributed to the effect of the treatment.

EXAMPLE 20

A 1971 field test of wheat (Blue Boy) consisted of 4.25 acres treated with *Bacillus uniflagellatus* as in Example 19. The results at harvest were recorded as:

| Control | Treated |
|---|---|
| 33.01 bu./acre | 48.74 bu./acre |

The difference of 15.73 bushels per acre amounts to a 47.6% increase attributed to the effect of the treatment. In this instance the planting was done on a rather poor shale type soil.

EXAMPLE 21

Another test of (Blue Boy) wheat in 1971 was conducted using 5.25 acres with 4 ounces of *Bacillus uniflagellatus* dust per acre treatment and 5.00 acres untreated as the control. The results at harvest were recorded as:

| Control | Treated |
|---|---|
| 65.27 bu./acre | 68.95 bu./acre |

The difference of 3.68 bushels per acre amounts to a 5.63% increase attributed to the effect of treatment. In this instance the soil was a high quality Hagerstown Loam. No observable stress on the wheat was evident during the entire growing season.

EXAMPLE 22

In 1972 a test of wheat (Blue Boy) was conducted with 52.75 acres of seed treated by mixing 6 ounces of the spore dust of *Bacillus uniflagellatus* per 100 pounds of seed in the drill box. The mixing was accomplished by placing the seed in the drill box, sprinkling the dust over it and stirring with a stick. The remaining 129.5 acres of the field was maintained as a control. The grain was combined and weighed to obtain the results as:

| Control | Treated |
|---|---|
| 5098 bushels | 2440 bushels |
| 39.36 bu./acre | 46.25 bu./acre |

This represents an increase of 6.89 bushels per acre or a 17.2% improvement attributed to the effect of the treatment.

EXAMPLE 23

Another 1972 test of wheat (Red Coat) was conducted as described in Example 22 using 16 acres of treatment with *Bacillus uniflagellatus* and the remaining 20 acres of the field maintained as the control. The total crop was harvested and weighed as:

| Control | Treated |
|---|---|
| 420 bushels | 400 bushels |
| 21 bu./acre | 25 bu./acre |

This represents an increase of one 4 bushels per acre, but it constitutes a 19% increase attributed to the effect of the treatment.

EXAMPLE 24

Another test of Red Coat wheat in 1972 was somewhat more extensive. The area treated with *Bacillus uniflagellatus* amounted to 49 acres while 72 acres were maintained as a control. When the crop was harvested and weighed, the results were recorded as:

| Control | Treated |
|---|---|
| 1030 bushels | 990 bushels |
| 14.3 bu./acre | 20.2 bu./acre |

On this section the increased yield was 5.9 bushels per acre showing a 27.2% increase attributed to the effect of the treatment.

EXAMPLE 25

Another 1972 test of Red Coat wheat with 52.5 acres treated with *Bacillus uniflagellatus* as a drill box mix was conducted with 58.5 acres maintained as the control. The yields in this instance were recorded as:

| Control | Treated |
|---|---|
| 1110 bushels | 1350 bushels |
| 18.95 bu./acre | 25.71 bu./acre |

The increase of 6.76 bushels per acre or 30.1% extra yield is attributed to the effect of the treatment.

The 1972 wheat harvests again demonstrate the pattern of greatest percentage improvement under the poorest growing conditions. In 1971 results we see the yields in the 65 bushels per acre range only increased by 5 to 6 percent. In controls of 33 bushels per acre range the improvement exceeded 45 percent. The tests in 1972 show the same trend. With the control plots approaching 40 bushels per acre, the improvement was only about 17 percent. With controls yielding barely 30 bushels per acre, the improvement reached 30 percent. The year 1972 was not a good year for wheat in Pennsylvania where the aforesaid test was conducted.

EXAMPLE 26

A field containing 4 acres was planted with treated (Ceresan) Pioneer 3304 corn. Half of the field was planted with seed additionally treated by drum tumbling with 4 ounces of spore dust of *Bacillus uniflagellatus* per 100 pounds of seed. The other 2 acres were planted with the same standard seed not treated with *Bacillus uniflagellatus*. The planting was in 38 inch rows with 7 inch spacing which approximates 23,500 seeds per acre. Seven samples consisting of 30 feet of row per sample were hand harvested from both the treated and control plots. The counts and weights were recorded as:

| Sample # | Control | | Treated | |
|---|---|---|---|---|
| | Ears | Weight | Ears | Weight |
| 1 | 39 | 19.25 | 50 | 26.25 |
| 2 | 47 | 24.15 | 49 | 25.25 |
| 3 | 37 | 16.35 | 47 | 24.50 |
| 4 | 38 | 19.50 | 50 | 26.00 |
| 5 | 48 | 23.50 | 48 | 24.25 |
| 6 | 47 | 24.25 | 48 | 24.75 |
| 7 | 46 | 22.75 | 49 | 26.75 |
| Totals | 302 | 149.79 | 341 | 177.75 |

The plant population for the control plot was indicated at 19,715 per acre while the treated plot showed 22,328 plants per acre. The average weight per ear from the control plot shows 0.495 lbs. per ear while the ears from the treated plot show 0.521 lbs. per ear.

EXAMPLE 27

An 8 acre field was planted with oats (Garry). Half of the field was treated with spore dust of *Bacillus uniflagellatus* and the other half maintained as the control. The harvest showed the yields to be almost identical with only a 0.1% increase in favor of the treatment. No particular stress was observed during the growing season. I presently believe that with oats, significant improvements are observable only under stress planting conditions.

EXAMPLE 28

The following tables represent replicated work on 18 varieties of wheat under extreme stress conditions. The plantings were done in the area of Presho, South Dakota with winter wheat. In this area, a yield of 20 to 30 bushels of wheat per acre is considered normal. The replications were done in test plots, each of which was 100 feet long and 6 feet wide, with 2 replications per variety of wheat being done.

The wheat was planted in September, 1972 and harvested in July, 1973. The wheat was stressed due to heavy winter rains and hard freezes and the absence of an appreciable snow cover. Moreover, the wheat was subjected to a severe attack by the green bug species of aphids.

The following tables demonstrate the yield, based against the control designated "Check". The "Lodging" was measured on a scale of 1 to 10, with 1 meaning that all of the plants remained standing, and 10 meaning that all of the plants were flat.

Influence of Seed Treatment (*Bacillus uniflagellatus*) on Grain Yield and other Agronomic characteristics of Selected Winter Wheat Varieties - South Central Research Station, Presho, South Dakota - 1973.

| Variety | Treatment | Percent Survival | Height Inches | Lodging (1-10) | Percent Moisture | Test Weight Lbs/Bu | Grain Yield Bu/Acre | Percent of Check |
|---|---|---|---|---|---|---|---|---|
| Bronze | Check | 45 | 32 | 1.2 | 10.5 | 55.5 | 12.5 | |
| | Bacillus | 70 | 32 | 1.2 | 10.3 | 54.5 | 16.6 | 133 |
| Centurk | Check | 48 | 30 | 1.0 | 13.5 | 58.0 | 19.8 | |
| | Bacillus | 60 | 31 | 1.0 | 13.0 | 58.5 | 26.4 | 133 |
| Eagle | Check | 42 | 31 | 1.0 | 12.2 | 58.0 | 17.8 | |
| | Bacillus | 48 | 29 | 1.0 | 13.2 | 56.0 | 22.6 | 127 |
| Froid | Check | 38 | 32 | 1.0 | 12.4 | 53.5 | 9.7 | |
| | Bacillus | 70 | 38 | 1.0 | 12.5 | 53.5 | 15.8 | 163 |
| Gage | Check | 62 | 34 | 1.0 | 12.0 | 55.0 | 19.8 | |
| | Bacillus | 80 | 32 | 1.0 | 12.8 | 55.5 | 23.6 | 119 |
| Guide | Check | 65 | 35 | 1.2 | 11.9 | 57.5 | 12.2 | |
| | Bacillus | 85 | 32 | 1.2 | 12.6 | 58.5 | 28.6 | 234 |
| Hume | Check | 80 | 35 | 1.2 | 12.2 | 56.0 | 22.7 | |
| | Bacillus | 72 | 34 | 1.2 | 12.5 | 56.0 | 22.4 | 99 |
| Lancer | Check | 46 | 31 | 1.0 | 11.6 | 56.5 | 15.8 | |
| | Bacillus | 66 | 32 | 1.0 | 12.6 | 56.8 | 23.5 | 149 |
| Omaha | Check | 55 | 30 | 1.0 | 12.2 | 57.5 | 18.0 | |
| | Bacillus | 88 | 32 | 1.0 | 11.7 | 60.0 | 28.2 | 157 |
| Scoutland | Check | 82 | 32 | 1.0 | 12.5 | 58.5 | 25.1 | |
| | Bacillus | 88 | 32 | 1.0 | 12.7 | 58.0 | 29.7 | 118 |
| Scout 66 | Check | 62 | 32 | 1.2 | 11.6 | 57.0 | 9.6 | |
| | Bacillus | 65 | 32 | 1.0 | 11.9 | 59.0 | 20.7 | 216 |
| Shawnee | Check | 78 | 34 | 1.0 | 11.6 | 57.5 | 23.0 | |
| | Bacillus | 80 | 34 | 1.0 | 11.7 | 57.5 | 25.5 | 111 |
| S.D. 7117 | Check | 40 | 32 | 1.2 | 12.6 | 56.5 | 17.2 | |
| | Bacillus | 50 | 30 | 1.2 | 12.2 | 54.5 | 19.8 | 115 |
| Trader | Check | 75 | 36 | 1.0 | 12.2 | 55.0 | 25.8 | |
| | Bacillus | 85 | 38 | 1.0 | 11.4 | 57.5 | 29.2 | 113 |
| Trapper | Check | 80 | 35 | 1.0 | 12.0 | 56.5 | 26.4 | |
| | Bacillus | 86 | 35 | 1.0 | 11.6 | 55.0 | 30.2 | 114 |
| Triumph | Check | 85 | 36 | 1.0 | 11.4 | 58.5 | 34.0 | |
| | Bacillus | 90 | 35 | 1.0 | 12.4 | 59.0 | 38.1 | 112 |
| Weathermaster 106 | Check | 45 | 33 | 1.5 | 13.4 | 59.0 | 18.0 | |
| | Bacillus | 65 | 36 | 1.2 | 12.5 | 58.4 | 22.0 | 122 |
| Winoka | Check | 55 | 39 | 1.2 | 12.4 | 56.5 | 19.3 | |
| | Bacillus | 71 | 40 | 1.0 | 12.4 | 57.0 | 23.0 | 119 |

I have established that spores of *Bacillus uniflagellatus* are effective against a wide variety of plant pathogens and, in particular, root pathogens, such as those of the genera Rhizoctonia, Verticillium, Pythium and Fusarium.

I have found that the beneficial results from spores of *Bacillus uniflagellatus* are effective in a wide variety of soils including sandy soils, adobe soils, loam soils, soils of low pH, and soils of high pH.

While I do not wish to be bound by any mechanism, I have noted the rapid formation of melanin in the roots of wheat plants being treated with the spores of *Bacillus uniflagellatus*. This melanin appears to act as a shield against penetration by parasites of a wide variety of types. Possibly, this same mechanism of early melanin formation occurs with other plants.

I believe that the method for increasing the yield of crops by treating plants with spores of *Bacillus uniflagellatus* has prime utility under conditions of stress. Thus, a plant growing under absolutely ideal conditions is limited in production only by its genetic capability. In practice, however, plant growing conditions seldom approach the ideal, and for most plant species, ideal conditions are not even established. Highly variable are the specific conditions of soil, its pH, its micro and macro nutrients, its bacterial, algal, fungal, nematodal, and larval content, its humus content and friability, percentages of decay in the vegetative residues, the amount of insect activity, the constantly changing moisture content, and the cycles of temperature. In addition to these natural variables, one must add the effects of chemicals used as pesticides, herbicides and fertilizers, and the proximity of other plants of the same or of different species (weeds) both by root zone competition and shading effect.

Where the plant is subjected to stress, the method of the present invention gives maximum utility.

In extensive testing, I have observed no toxicity to mammals attributable to the *Bacillus uniflagellatus*.

*Bacillus uniflagellatus* does not persist in the soil after the crops are removed. To demonstrate this, cotton, peanuts, grain sorghum and soybeans were planted in test plots on the College Farm of Eastern New Mexico University. In that area all these crops require irrigation. As the plants grew, tests were run on samples of root and soil masses from *Bacillus uniflagellatus* treated and control plots. In the treated plants, the *Bacillus uniflagellatus* was recovered in very high numbers throughout the growing season. In some instances, notably cotton and peanuts, the *Bacillus uniflagellatus* was the predominant organism recovered from dilutions of the macerated root and soil mass.

After the crops were removed, the land remained idle until preparation began for the next crop. At this time irrigation was resumed to provide moisture for plowing and tillage. Soil samples were again taken from treated and control plots, and dilutions were run. In not one instance was the *Bacillus uniflagellatus* recovered. The soil microorganisms were, for all practical purposes, identical between the treated and control areas.

While the aforesaid example involved a special case, namely the withholding of irrigation prior to the crop removal and no appreciable growth of weeds, so that the *Bacillus uniflagellatus* is destroyed by competitive soil-borne organisms within a matter of weeks, yet it demonstrates that the persistency of *Bacillus uniflagellatus* in the soil is not great. Work on fallow fields with a wide variety of crops has demonstrated that *Bacillus uniflagellatus* does not persist from one growing season to another in the soil. It is, of course, possible for some limited survival of *Bacillus uniflagellatus* to occur in the soil, such as due to the presence of weeds following a grain harvest in moist areas, with the exudate from the roots of the weeds stimulating the growth of the *Bacillus uniflagellatus.* However, no adverse affect will occur from this.

Soil applications of *Bacillus uniflagellatus* prior to planting are wasteful, since only those spores adjacent to germinating seed would grow and protect the plant.

The present invention may be embodied in other specific forms without departing from the spirit or essential attributes thereof and, accordingly, reference should be made to the appended claims, rather than to the foregoing specification as indicating the scope of the invention.

I claim:

1. A method for increasing the yield of food crops which comprises treating a food crop yielding plant with a plant treating agent consisting essentially of an effective amount of spores of *Bacillus uniflagellatus* (ATCC No. 15,134), said spores being applied to the plant in such a manner that the spores will eventually come into contact with exudates produced by the roots of the plant, said plant being one which does not have a single large taproot, with no appreciable branching of the root.

2. A method in accordance with claim 1 in which the *Bacillus uniflagellatus* spores are commingled with the seeds of the plant, prior to the planting of such seeds.

3. A method in accordance with claim 1 in which the *Bacillus uniflagellatus* spores are adhesively secured to the seeds of the plant, prior to the planting of such seeds.

4. A method in accordance with claim 1 in which the spores of the *Bacillus uniflagellatus* are coated with antibiotic produced in a culture of *Bacillus uniflagellatus.*

5. A method in accordance with claim 1 in which the plant is a food crop selected from the group consisting of barley, rice, wheat, corn, oats, bush beans, alfalfa, lettuce, castor beans, melon, strawberries, boysenberries, avocado, raspberries, peas, onions, rhubarb, blackberries, blueberries, zucchini, radishes, carrots, brussel sprouts, cucumbers, peanuts, pepper, tomatoes, cantaloupe, Garbanzo beans, Irish potatoes, sorghum, cotton, mushrooms, cocoa, soy beans, oranges, lemons, grapefruit, limes, and peaches.

6. A method in accordance with claim 2 in which the plant is a food crop selected from the group consisting of barley, rice, wheat, corn, oats, bush beans, alfalfa, lettuce, castor beans, melon, strawberries, boysenberries, avocado, raspberries, peas, onions, rhubarb, blackberries, blueberries, zucchini, radishes, carrots, brussel sprouts, cucumbers, peanuts, pepper, tomatoes, cantaloupe, Garbanzo beans, Irish potatoes, sorghum, cotton, mushrooms, cocoa, soy beans, oranges, lemons, grapefruit, limes, and peaches.

7. A method in accordance with claim 3 in which the plant is a food crop selected from the group consisting of barley, rice, wheat, corn, oats, bush beans, alfalfa, lettuce, castor beans, melon, radishes, avocado, peas, onions, carrots, brussel sprouts, cucumbers, peanuts, pepper, zucchini, tomatoes, cantaloupe, Garbanzo beans, sorghum, cotton, soy beans, oranges, lemons, grapefruit and limes.

8. A method in accordance with claim 1 in which the crop is subjected to stress during its growing cycle.

9. A method according to claim 3 wherein the spores are applied to the seeds of the plant in an amount of at least about 25 to 100 spores per seed.

10. A method in accordance with claim 1 wherein the *Bacillus uniflagellatus* spores are suspended in an aqueous medium and the root system of the plant is treated with such suspension.

11. A method according to claim 1 wherein the *Bacillus uniflagellatus* spores are mixed into the soil immediately surrounding the root system of the plant.

12. A method according to claim 1 wherein the *Bacillus uniflagellatus* spores are sprayed onto the leaves of the plant and washed into the soil immediately surrounding the plant.

13. A substantially uniform mixture of a blend consisting essentially of seeds of a plant which upon cultivation yields a food crop and an effective food crop yield-increasing amount of spores of *Bacillus uniflatellatus* (ATCC No. 15,134).

14. A mixture in accordance with claim 13, in which the *Bacillus uniflagellatus* spores are adhesively secured to the seeds of the plant.

15. A mixture in accordance with claim 14 in which at least about 25 to 100 spores of *Bacillus uniflagellatus* spores are adhesively secured to each of the seeds of the plant.

16. A mixture in accordance with claim 14 in which the plant is a food crop selected from the group consisting of barley, rice, wheat, corn, oats, bush beans, alfalfa, lettuce, castor beans, melon, radishes, avocado, peas, onions, carrots, brussel sprouts, cucumbers, peanuts, pepper, zucchini, tomatoes, cantaloupe, Garbanzo beans, sorghum, cotton, soy beans, oranges, lemons, grapefruit and limes.

17. A mixture in accordance with claim 13 in which the *Bacillus uniflagellatus* spores are coated with antibiotic produced in a culture of *Bacillus uniflagellatus.*

18. A mixture in accordance with claim 13 in which the seeds are coated with a conventional chemical fungicide which is substantially inert to *Bacillus uniflagellatus,* whereby the seeds are protected until the spores germinate and commence releasing antibiotic.

19. A mixture in accordance with claim 13 in which the spores are uniformly dispersed on solids derived from the drying of the culture medium used to grow the spores of *Bacillus uniflagellatus.*

20. A mixture in accordance with claim 19 in which the plant is a food crop selected from the group consisting of barley, rice, wheat, corn, oats, bush beans, alfalfa, lettuce, castor beans, melon, strawberries, boysenberries, avocado, raspberries, peas, onions, rhubarb, blackberries, blueberris, zucchini, radishes, carrots, brussel sprouts, cucumbers, peanuts, pepper, tomatoes, cantaloupe, Garbanzo beans, Irish potatoes, sorghum, cotton, mushrooms, cocoa, soy beans, oranges, lemons, grapefruit, limes, and peaches.

21. A mixture useful for the treatment of food crop yielding plants to increase their yield and utilization of their growth potential consisting essentially of a powder of an effective amount of spores of *Bacillus uniflagellatus (ATCC No.* 15,134) substantially uniformly dispersed on a powdered carrier for said spores, said mixture having no more than ten weight percent water.

22. A mixture according to claim 21 wherein the powdered carrier is substantially non-toxic to the *Bacillus uniflagellatus* and to the plants being treated.

23. A mixture according to claim 22 wherein the spores are present in the carrier in an amount of approximately 100,000 to 300,000,000 spores per gram of mixture.

24. A mixture according to claim 23 wherein the spores are present in the carrier in an amount of approximately 3,000,000 to 50,000,000 spores per gram of mixture.

25. A mixture according to claim 21 containing no less than 4 weight percent water.

26. A mixture according to claim 24 containing no less than 4 weight percent water.

27. A method for increasing the yield of crops which comprises treating a food crop yielding plant with the mixture according to claim 21.

28. A method for increasing the yield of crops which comprises treating a food crop yielding plant with the mixture according to claim 22.

29. A method for increasing the yield of crops which comprises treating a food crop yielding plant with the mixture according to claim 23.

30. A method for increasing the yield of crops which comprises treating a food crop yielding plant with the mixture according to claim 24.

31. A method for increasing the yield of crops which comprises treating a food crop yielding plant with the mixture according to claim 25.

32. A method for increasing the yield of crops which comprises treating a food crop yielding plant with the mixture according to claim 26.

33. A method for increasing the amount of protein derived from a plant selected from the group of plants consisting of wheat, barley, oats, and corn which comprises treating said plant, in a soil containing excess nitrogen over that normally used to cultivate the plant, with a plant treating agent consisting essentially of an effective amount of spores of *Bacillus uniflagellatus* (ATCC No. 15,134) whereby a crop is obtained which contains a higher weight percentage of protein than is normally obtained, said spores being applied to the plant in such a manner that the spores will eventually come into contact with exudates produced by the roots of the plant.

34. A method in accordance with claim 33 in which the spores are uniformly dispersed on a powdered carrier which is substantially non-toxic to *Bacillus uniflagellatus* and to the plant being treated.

35. A method in accordance with claim 34 wherein the mixture of spores and carrier contains between 100,000 to 300,000,000 spores per gram of mixture.

36. A method in accordance with claim 35 wherein the mixture of spores and carrier contains between 3,000,000 and 50,000,000 spores per gram of mixture.

37. A method for forming a mixture useful for increasing the yield of food crop yielding plants which comprises blending together ingredients consisting essentially of seeds of a food crop yielding plant, an effective amount of spores of *Bacillus uniflagellatus*, and an inert adhesive, said inert adhesive being mechanically admixed with the spores and seeds whereby the spores are adhesively secured to the seeds.

38. A method in accordance with claim 37 in which the plant is a food crop selected from the group consisting of barley, rice, wheat, corn, oats, bush beans, alfalfa, lettuce, castor beans, melon, radishes, avocado, peas, onions, carrots, brussel sprouts, cucumbers, peanuts, pepper, zucchini, tomatoes, cantaloupe, Garbanzo beans, sorghum, cotton, soy beans, oranges, lemons, grapefruit and limes.

* * * * *